United States Patent
Liu et al.

(10) Patent No.: US 10,857,186 B2
(45) Date of Patent: Dec. 8, 2020

(54) TRADITIONAL CHINESE MEDICINE COMPOSITION FOR TREATING ACUTE STAGE OF CEREBRAL INFARCTION

(71) Applicant: Jiangsu Province Institute of Traditional Chinese Medicine, Nanjing (CN)

(72) Inventors: Hongquan Liu, Nanjing (CN); Xiaolan Cheng, Nanjing (CN); Jingbo Li, Nanjing (CN); Mingming Fang, Nanjing (CN); Shuting Jiang, Nanjing (CN); Yudi Lu, Nanjing (CN); Jie Gong, Nanjing (CN)

(73) Assignee: Jiangsu Province Institute of Traditional Chinese Medicine, Nanjing (CN)

( * ) Notice: Subject to any disclaimer, the term of this patent is extended or adjusted under 35 U.S.C. 154(b) by 0 days.

(21) Appl. No.: 16/816,188

(22) Filed: Mar. 11, 2020

(65) Prior Publication Data

US 2020/0215119 A1    Jul. 9, 2020

Related U.S. Application Data

(63) Continuation-in-part of application No. 16/265,852, filed on Feb. 1, 2019.

(51) Int. Cl.
| | |
|---|---|
| *A61K 35/32* | (2015.01) |
| *A61K 36/882* | (2006.01) |
| *A61K 36/9066* | (2006.01) |
| *A61P 9/10* | (2006.01) |
| *A61K 36/65* | (2006.01) |
| *A61K 36/64* | (2006.01) |

(52) U.S. Cl.
CPC .............. *A61K 35/32* (2013.01); *A61K 36/64* (2013.01); *A61K 36/65* (2013.01); *A61K 36/882* (2013.01); *A61K 36/9066* (2013.01); *A61P 9/10* (2018.01); *A61K 2236/333* (2013.01)

(58) Field of Classification Search
None
See application file for complete search history.

(56) References Cited

U.S. PATENT DOCUMENTS 8,808,768 B2 * 8/2014 Agarwal ............ A61K 36/9066
424/756

FOREIGN PATENT DOCUMENTS

| CN | 101721572 B | * | 5/2011 |
| CN | 106110178 A | * | 11/2016 |

* cited by examiner

*Primary Examiner* — Susan Hoffman
(74) *Attorney, Agent, or Firm* — CBM Patent Consulting, LLC

(57) ABSTRACT

A traditional Chinese medicine composition for treating acute stage of cerebral infarction. The traditional Chinese medicine composition combines buffalo horns, unprocessed rehmannia roots, red paeony roots, cortex moutan, grassleaf sweelflag rhizome and turmeric root-tuber, and exerts the synergistic effects of the medicines through compatibility, thereby being capable of more effectively clearing away heat and toxic materials, cooling the blood, dissipating blood stasis and inducing resuscitation, and achieving the purpose of treating acute stage of cerebral infarction.

7 Claims, No Drawings

TRADITIONAL CHINESE MEDICINE COMPOSITION FOR TREATING ACUTE STAGE OF CEREBRAL INFARCTION

This application is continuation in part of U.S. Ser. No. 16/265,852 filed on 1 Feb. 2019 now abandoned, that claimed priority to Chinese Patent Application Ser. No. CN201810893930.2 filed on 8 Aug. 2018.

TECHNICAL FIELD

The present invention relates to a traditional Chinese medicine composition for treating acute stage of cerebral infarction and a preparation thereof, and belongs to the technical field of traditional Chinese medicine.

BACKGROUND ART

Cerebral infarction (CI) is a general term for ischemic stroke, including cerebral thrombosis, lacunar infarction, cerebral embolism and the like, and accounts for about 70% of all cerebral strokes and is a brain lesion caused by cerebral blood supply disorders. In China, the CI has the characteristics of high incidence, high mortality, high disability rate and high recurrence rate. The CI has become the first cause of death and disability in China, and an important factor known to cause a high disability rate of the CI in the medical field is the neglect of rehabilitation in the acute stage of the CI. Poor rehabilitation results cause many sequelae, such as hemiplegia, hemi-physical disabilities, limb numbness, hemianopia and aphasia, thereby bringing heavy economic burden to patient families and the society.

The majority of patients suffer from progressive CI which is clinically divided into four stages according to courses of the disease: a resurgence time window stage (within 6 hours of symptoms), an acute stage (2-4 weeks), a recovery stage (1-6 months) and a stage of sequelae (more than 6 months). Modern studies show that dissolution of blood clots and recovery of blood supply are the most reasonable treatment methods. Because thrombolytic treatment has a certain 'time window', some studies suggest that the thrombolytic treatment effect is obvious within 3-6 hours (namely the resurgence time window stage of the CI). However, due to the problems of uncertain onset time, unclear patient judgment, long hospitalizing and diagnosing time and the like of the disease, the majority of patients are difficult to be treated in time during the resurgence time window, and the treatment in the acute stage of the CI is the most critical stage affecting the prognosis of the patients.

In acute stage of the CI, the degree of disease is different and rehabilitation is very difficult. Some patients may have neurological deterioration, and no unified rehabilitation operation specifications or consensus are provided at present. The CI is divided into main types of cerebral thrombosis, cerebral embolism, lacunar infarction and the like according to different pathogenic mechanisms. Because the main pathogenesis of cerebral thrombosis is atherosclerosis, the cause of atherosclerosis is the most common pathogenesis of the CI.

The CI is also known as stroke in the field of traditional Chinese medicines. It has a long history of treatment and rich clinical experience in China. With the continuous development of the modern traditional Chinese medicine theory and the updating of the technical means, the research on the action mechanism of traditional Chinese medicines in treatment of the CI has been deepening, and the status of treatment has been also widely accepting by the international community. The optimized combination of different traditional Chinese medicine treatment methods can effectively improve the functional recovery rate and reduce the disability rate of the patients after the CI, and has been widely applied as the conventional treatment of the CI clinically. Based on the syndrome differentiation theory and the clinical experience of the traditional Chinese medicine, the present invention provides a selection scheme for clinicians. The composition is reasonable in compatibility of components, good in clinical treatment effect, small in toxic and side effects, low in prescription cost, can reduce the pain and economic burden of the patients.

SUMMARY OF THE INVENTION

The objective of the present invention is to provide a traditional Chinese medicine composition for treating acute stage of cerebral infarction with high effect-taking speed, good curative effects and no side effects.

Another objective of the present invention is to provide a preparation method of the traditional Chinese medicine composition.

The objectives of the present invention are achieved by the following measures:

The traditional Chinese medicine composition for treating acute stage of cerebral infarction is prepared from the following raw materials in parts by weight: 10-50 parts of buffalo horns, 10-30 parts of unprocessed rehmannia roots, 10-30 parts of red paeony roots, 10-30 parts of cortex moutan, 6-20 parts of grassleaf sweetflag rhizome and 10-30 parts of turmeric root-tuber.

Preferably, the traditional Chinese medicine composition for treating acute stage of cerebral infarction is prepared from the following raw materials in parts by weight: 10-30 parts of buffalo horns, 10-20 parts of unprocessed rehmannia roots, 10-20 parts of red paeony roots, 10-20 parts of cortex moutan, 6-15 parts of grassleaf sweetflag rhizome and 10-20 parts of turmeric root-tuber.

The traditional Chinese medicine composition is formulated into various preparations with pharmaceutically acceptable adjuvant materials, such as decoction, granules, capsules, tablets and the like, and the preferable preparation is granules.

The preparation method of the traditional Chinese medicine composition for treating acute stage of cerebral infarction comprises the following steps: mixing herbal pieces of the buffalo horns, the unprocessed rehmannia roots, the red paeony roots and the cortex moutan and performing water extraction; mixing herbal pieces of the grassleaf sweetflag rhizome and the turmeric root-tuber and performing extraction by hot reflux with 70% ethanol; separately concentrating the water extract and the ethanol extract, and performing combining, spray drying and uniform mixing to prepare the traditional Chinese medicine composition.

By the water extraction method, water extraction is performed for 2-3 times with 1-3 h each time, and the amount of water is 8-10 times of the total weight of the medicinal materials.

By the ethanol extraction method, extraction is performed with 70% ethanol for 2-3 times with 1-2 h each time, and the amount of ethanol is 8-10 times of the total weight of the medicinal materials.

A clear paste obtained by concentration can be granulated by spray drying. Specifically, the clear paste is spray-dried to obtain fine powder, and the fine powder is granulated by adding dextrin.

The granules are prepared into wet granules by using dextrin, and performed screening with a 18-20 mesh sieve, dried, granulated, screened again, and packaged.

The capsules are prepared by uniformly mixing magnesium oxide, calcium hydrogen phosphate, starch, magnesium stearate and other adjuvant materials with dried fine powder, and filling capsules with the mixture.

The tablets are prepared by uniformly mixing sugar powder, microcrystalline cellulose, magnesium stearate, calcium carbonate and other adjuvant materials with dried fine powder, granulating the mixture by a wet process, and performing drying and tablet pressing.

Compared with the existing technology, the present invention has the following obvious advantages:

First of all, the traditional Chinese medicine composition used in the present invention is developed according to the characteristics of the pathogenesis of the acute stage of cerebral infarction, has no obvious toxic and side effects, and has high safety factor compared with the same type of chemical medicines. The medicinal properties and characteristics of the prescription are as follows:

The buffalo horns are a monarch drug, are bitter and salty in taste and cold in nature, enter the heart, liver, spleen and stomach, can clear the heart and liver and relieve heat toxin, are cold but not suppressing, straightly enter the blood and cool the blood.

The unprocessed rehmannia roots and the red paeony roots are ministerial drugs. The unprocessed rehmannia roots are sweet and bitter in taste and cold in nature, enter the heart, liver and kidney, can be used for clearing away heat, cooling blood, nourishing Yin, promoting the production of body fluid, restoring Yin and blood and stopping bleeding. The red paeony roots are bitter in taste and slightly cold in nature, enter the liver, can clear heat, cool the blood, dissipate blood stasis and relieve pain, and are widely used for body heat and bleeding and redness and swelling of the eyes due to invasion of the blood system by heat in epidemic febrile disease. The red paeony roots and rehmannia roots together can assist the buffalo horns to resolve excess heat in the blood system together.

The cortex moutan, the grassleaf sweetflag rhizome and the turmeric root-tuber are adjuvant drugs. The cortex moutan is bitter in taste and slightly cold in nature, can clear away heat and cool blood, promote blood circulation and disperse stasis, and play the role of removing ecchymoses and dispersing stasis. The grassleaf sweetflag rhizome is acrid and bitter in taste and warm in nature, enters the heart and stomach, can induce resuscitation, eliminate phlegm, refresh mind and promote mentality, and is used for unconsciousness, epilepsy and apoplectic disease. The turmeric root-tuber is acrid and bitter in taste and cold in nature, enters the liver, heart and lung, can promote the circulation of qi, disperse stasis, clear away the heart-fire and relieve the depressed liver, and is used for fever, unconsciousness, epilepsy and madness. The six medicines are combined to play the role of clearing away heat and toxic material, cooling blood, dissipating blood stasis and inducing resuscitation.

The present invention adopts the buffalo horns, the unprocessed rehmannia roots, the red paeony roots, the cortex moutan, the grassleaf sweetflag rhizome and the turmeric root-tuber as main raw materials, and extracts the effective parts thereof with medicinal value for preparing a preparation, and the preparation has the effects of removing heat to cool blood, dissipating blood stasis and inducing resuscitation. Therefore, the traditional Chinese medicine composition of the present invention can be applied to preparation of a medicine for treating the acute stage of cerebral infarction.

The present invention is an empirical prescription summarized in perennial clinical practice. There is no incompatibility in this prescription, and the amount of use is within the prescribed scope of the Pharmacopoeia. No toxic and side effects are found in long-term clinical use.

Secondly, the traditional Chinese medicine composition of the present invention has obvious curative effect feedback in clinical use, and shown by clinical observation performed by the inventors on 2 courses of treatment, in a treatment group, 13 cases are basically cured, 32 cases are significantly improved and 11 cases are improved, the marked effective rate is 70.59%, and the effective rate is 96.55%; in a control group, 8 cases are cured, 22 cases are significantly improved, 16 cases are improved, the marked effective rate is 52.63%, and the effective rate is 80.70%. There are significant differences between the two groups in the marked effective rate and the effective rate ($P<0.05$, the treatment group is significantly better than the control group). The National Institute of Health Stroke Scale (NIHSS) scores of both the treatment group and the control group after treatment are improved, and the difference is statistically significant ($P<0.05$) compared with admission. However, the treatment group is more significant than the control group, and the overall clinical effect has significant difference compared with the control group.

DETAILED DESCRIPTION OF THE INVENTION

The present invention is further illustrated by the following examples. The specific details of the examples are merely illustrative of the present invention and shall not be construed as limitations of the general technical scheme of the present invention. In the following examples, each part by weight is 1 gram.

Example 1

Preparation of decoction:

weighing the following crude drugs of the present invention in parts by weight: 30 grams of buffalo horns, 15 grams of unprocessed rehmannia roots, 15 grams of red paeony roots, 10 grams of cortex moutan, 10 grams of grassleaf sweetflag rhizome and 10 grams of turmeric root-tuber;

weighing herbal pieces of the traditional Chinese medicine components according to the proportions, adding 4 times of water for the first time, performing soaking for 1 h, performing decocting for 2 h, adding 3 times of water for the second time, performing decocting for 1.5 h, adding 3 times of water for the third time, performing decocting for 1.5 h, separately filtering decoctions and combining the decoctions.

When the traditional Chinese medicine composition of the present invention is used for treating the acute stage of cerebral infarction, one dose of the prepared decoction is administered a day in 2-3 times.

Example 2

Preparation of granules:

weighing the following crude drugs of the present invention in parts by weight: 15 grams of buffalo horns, 12 grams of unprocessed rehmannia roots, 10 grams of red paeony roots, 12 grams of cortex moutan, 6 grams of grassleaf sweetflag rhizome and 12 grams of turmeric root-tuber.

weighing herbal pieces of the traditional Chinese medicine components according to the proportions, mixing herbal pieces of the buffalo horns, the unprocessed rehmannia roots, the red paeony roots and the cortex moutan, and performing water extraction, mixing herbal pieces of the grassleaf sweetflag rhizome and the turmeric root-tuber and performing extraction by hot reflux with 70% ethanol, separately concentrating the water extract and the ethanol extract, performing combining and filtering, taking supernatant liquid, adding dextrin to the supernatant liquid, performing granulating by a wet process, and performing drying and uniform mixing;

by the water extraction method, water extraction is performed for 3 times with 2 h each time, and the amount of water is 8 times of the total weight of the medicinal materials;

by the ethanol extraction method, extraction is performed with 70% ethanol for 3 times with 1.5 h each time, and the amount of ethanol is 8 times of the total weight of the medicinal materials;

combining and filtering the water extract and the ethanol extract, and performing concentration under reduced pressure on the filtrate until the relative density of clear paste is 1.1-1.2 at 75° C., where the rotation speed of a tubular bowl centrifuge is 5000 rpm.

When the traditional Chinese medicine composition of the present invention is used for treating the acute stage of cerebral infarction, one bag contains 5 g of the composition which is equivalent to 32.5 g of crude medicinal herbs, and 1 bag of the prepared granules is administered each time, 2 times a day.

Example 3

Preparation of capsules:
weighing the following crude drugs of the present invention in parts by weight: 20 grams of buffalo horns, 15 grams of unprocessed rehmannia roots, 12 grams of red paeony roots, 12 grams of cortex moutan, 6 grams of grassleaf sweetflag rhizome and 12 grams of turmeric root-tuber;

weighing herbal pieces of the traditional Chinese medicine components according to the proportions, mixing herbal pieces of the buffalo horns, the unprocessed rehmannia roots, the red paeony roots and the cortex moutan and performing water extraction, mixing herbal pieces of the grassleaf sweetflag rhizome and the turmeric root-tuber and performing extraction by hot reflux with 70% ethanol, separately concentrating the water extract and the ethanol extract, and performing combining, drying under vacuum reduced pressure, pulverizing, uniform mixing, adding of adjuvant materials, granulating, uniform mixing and filling of capsules;

by the water extraction method, water extraction is performed for 2 times with 2 h each time, and the amount of water is 10 times of the total weight of the medicinal materials;

by the ethanol extraction method, extraction is performed with 70% ethanol for 2 times with 1.5 h each time, and the amount of ethanol is 10 times of the total weight of the medicinal materials;

the pharmaceutical adjuvant materials comprise magnesium oxide, calcium hydrogen phosphate, starch and magnesium stearate.

When the traditional Chinese medicine composition of the present invention is used for treating the acute stage of cerebral infarction, one capsule contains 0.5 g of the composition which is equivalent to 7 g of crude medicinal herbs, and 3-4 of the prepared capsules are administered each time, 2-3 times a day.

Example 4

Preparation of tablets:
weighing the following crude drugs of the present invention in parts by weight: 15 grams of buffalo horns, 12 grams of unprocessed rehmannia roots, 12 grams of red paeony roots, 10 grams of cortex moutan, 10 grams of grassleaf sweetflag rhizome and 12 grams of turmeric root-tuber;

weighing herbal pieces of the traditional Chinese medicine components according to the proportions, mixing herbal pieces of the buffalo horns, the unprocessed rehmannia roots, the red paeony roots and the cortex moutan and performing water extraction, mixing herbal pieces of the grassleaf sweetflag rhizome and the turmeric root-tuber and performing extraction by hot reflux with 70% ethanol, separately concentrating the water extract and the ethanol extract, and performing combining, drying under vacuum reduced pressure, pulverizing, adding of sugar powder, granulating, adding of pharmaceutical adjuvant materials, uniform mixing, tablet pressing, drying and packaging;

by the water extraction method, water extraction is performed for 3 times with 1.5 h each time, and the amount of water is 9 times of the total weight of the medicinal materials;

by the ethanol extraction method, extraction is performed with 70% ethanol for 3 times with 1 h each time, and the amount of ethanol is 9 times of the total weight of the medicinal materials;

the pharmaceutical adjuvant materials comprise microcrystalline cellulose, magnesium stearate and calcium carbonate.

When the traditional Chinese medicine composition of the present invention is used for treating the acute stage of cerebral infarction, one tablet contains 0.4 g of the composition which is equivalent to 6 g of crude medicinal herbs, and 3-4 of the prepared tablets are administered each time, 2-3 times a day.

Example 5

The medicine composition prepared by the method of the example of the present invention is used for clinical trials:

1. Case selection: A total of 115 patients in the acute stage of cerebral infarction in a neurology department of a hospital are selected, including 61 males and 54 females; the oldest is 81 years old, the youngest is 66 years old, and the average age is 78.078±7.215 years old. The diagnostic criteria refer to the 2013 American Academy of Neurology (AAN) guidelines for the application of antithrombotic drugs for ischemic cerebrovascular disease, and the Chinese guidelines for the diagnosis and treatment of cerebral infarction with integrated Chinese and Western medicine (2017). All patients are scored according to the National Institutes of Health Stroke Scale (NIHSS) at admission. The above cases are randomly divided into 2 groups. There are no significant differences ($P>0.05$) in age, gender and condition between the two groups, which are comparable.

2. Treatment methods: The two groups of patients are divided into a control group and a treatment group. The control group received routine treatment, including regulation of the patients' blood pressure according to conditions, treatment with anti-platelet, fiber-reducing and intravenous thrombolytic drugs, observation of complications and expectant treatment on the disease, and combination with neurological function rehabilitation training. In the treatment group, in addition to the above-mentioned therapy, the decoction of the Example 1 is orally administered, the single prescription amount/day is administered in two times, the course of treatment is 14 days, and the course of treatment is continued for 2 courses.

3. Curative effect evaluation criteria: According to the changes of NIHSS scores before and after treatment, the curative effects of each group and the comparison between groups are evaluated. Curative effect evaluation criteria:
basic cure: NIHSS reduces by ≥90%;
significant improvement: NIHSS reduces by 46% to 89%;
improvement: NIHSS reduces by 18% to 45%;
no change: NIHSS reduces or increases by <18%;
deterioration: NIHSS increases by ≥18%.

Marked effective rate=basic cure rate+significant improvement rate; total effective rate=basic cure rate+significant improvement rate+improvement rate.

Statistical treatment is performed by using the t test and the Fisher test.

4. Comparison of clinical effects between the two groups is shown in Table 1:

TABLE 1

Comparison of the curative effects of two groups of patients in acute stage of cerebral infarction (example)

| Groups | Number of patients | Basic cure | Significant improvement | Improvement | No change | Deterioration |
|---|---|---|---|---|---|---|
| Control group | 57 | 8 | 22 | 16 | 9 | 2 |
| Treatment group | 58 | 13 | 32 | 11 | 1 | 1 |

From the above results, it can be seen that the improvement degree of NIHSS index in patients treated with additional use of the decoction of the present invention is significantly better than the control group, indicating that the use of conventional treatment with addition of the decoction can effectively improve restoration of neurological functions of patients in the acute stage of cerebral infarction, and can effectively reduce the incidence of sequelae.

The comparison of clinical curative effects of the two groups of patients is shown in Table 2:

TABLE 2

Comparison of clinical curative effects of two groups of patients

| Groups | Marked effective | Effective | No effect | Marked effective rate (%) | Effective rate (%) |
|---|---|---|---|---|---|
| Control group | 30 | 46 | 11 | 52.63 | 80.70 |
| Treatment group | 45 | 56 | 2 | 77.59 | 96.55 |

The comparison of NIHSS scores between the two groups is shown in Table 3:

TABLE 3

Comparison of NIHSS scores between 2 groups of patients

| Groups | Number of patients | Before treatment ($\bar{x} \pm s$) | After treatment ($\bar{x} \pm s$) |
|---|---|---|---|
| Control group | 57 | 15.65 ± 4.12 | 6.61 ± 2.24 |
| Treatment group | 58 | 15.16 ± 4.35 | 4.75 ± 1.87 |

As shown in the above table, the effective rate of the treatment group is 96.55%, the effective rate of the control group is 73.68%, and there is a significant difference between the two groups (P<0.05, the treatment group is significantly better than the control group). The marked effective rate of the treatment group is 77.59%, the marked effective rate is 52.63%, and there is significant difference between the two groups (P<0.05, the treatment group is significantly better than the control group). The above curative results show that the traditional Chinese medicine composition of the present invention has a good auxiliary effect on the restoration of neurological functions of patients in the acute stage of cerebral infarction and can be used together with clinical treatment to improve the clinical symptoms and physical signs of patients in the acute stage of cerebral infarction, demonstrating that the traditional Chinese medicine composition of the present invention has good curative effects on patients in the acute stage of cerebral infarction and has potential clinical application value.

Example 6

The medicine compositions prepared by the method of the example of the present invention and similar prescriptions are used for clinical controlled trials:

1. Case selection: A total of 307 patients in the acute stage of cerebral infarction in a neurology department of a hospital are selected, including 183 males and 124 females, wherein the oldest is 79 years old, the youngest is 65 years old, and the average age is 72.571±4.199 years old. The diagnostic criteria refer to the 2013 American Academy of Neurology (AAN) guidelines for the application of antithrombotic drugs for ischemic cerebrovascular disease, and the Chinese guidelines for the diagnosis and treatment of cerebral infarction with integrated Chinese and Western medicine (2017). All patients are scored according to the National Institutes of Health Stroke Scale (NIHSS) at admission. The above cases are randomly divided into seven groups. There are no significant differences (P>0.05) in age, gender and condition among the seven groups, which are comparable.

2. Treatment methods: The seven groups of patients are divided into a patent prescription treatment group and similar prescription treatment groups. On the basis that the patients of all the groups receive routine treatment, the blood pressure of the patients is regulated according to conditions, anti-platelet, fiber-reducing and intravenous thrombolytic drugs are adopted for treatment, complications of the patients are observed and expectant treatment is performed, and neurological function rehabilitation training is performed simultaneously. Specific prescriptions of different drug administration groups are shown in the following table. In the patent prescription treatment group, the decoction of the Example 1 is orally administered, the single prescription amount/day is administered in two times, the course of treatment is 14 days, and the course of treatment is continued for 2 courses. In the similar prescription treatment groups, decoctions are prepared through the method of the Example 1, the single prescription amount/day is administered in two times, the course of treatment is 14 days, and the course of treatment is continued for 2 courses.

| Groups | Prescriptions |
| --- | --- |
| Patent prescription treatment group | 30 grams of buffalo horn, 15 grams of radix *rehmanniae*, 15 grams of red paeony root, 10 grams of cortex moutan, 10 grams of rhizoma *acori tatarinowii* and 10 grams of radix *curcumae* |
| Similar prescription treatment group 1 | 30 grams of buffalo horn, 15 grams of radix *rehmanniae*, 10 grams of cortex moutan, 15 grams of red paeony root, 6 grams of flos caryophylli and 10 grams of semen *persicae* |
| Similar prescription treatment group 2 | 30 grams of buffalo horn, 10 grams of rhizoma *curcumae longae*, 15 grams of radix *salviae miltiorrhizae*, 15 grams of herba leonuri, 10 grams of radix *lithospermi* and 10 grams of radix *curcumae* |
| Similar prescription treatment group 3 | 30 grams of buffalo horns, 15 grams of radix *rehmanniae*, 6 grams of frankincense, 10 grams of concretio silicea *bambusae*, 15 grams of red paeony root and 10 grams of cortex moutan |
| Similar prescription treatment group 4 | 30 grams of buffalo horn, 10 grams of radix *rubiae*, 15 grams of radix *cyathulae*, 6 grams of radix *notoginseng*, 6 grams of pollen *typhae* and 10 grams of herba seu radix *cirsii* japonici |
| Control group 1 (CN106110178A) | 3 grams of benzoin, 12 grams of rhizoma *acori tatarinowii*, 12 grams of ursine seal's penis and teste, 12 grams of semen *cuscutae*, 12 grams of fennel, 24 grams of radix *achyranthes bidentatae*, 12 grams of frankincense, 12 grams of rhizoma *curcumae longae*, 3 grams of herba asari, 12 grams of radix *angelicae sinensis*, 12 grams of myrrh, 12 grams of safflower, 9 grams of cortex moutan, 12 grams of Japanese polypody rhizome, 12 grams of *aloe vera*, 6 grams of cortex *cinnamomi* and 12 grams of radix *cynanchi* atrati |
| Control group 2 (CN101721572A) | 15 grams of radix et rhizoma rhei, 40 grams of buffalo horn, 15 grams of red paeony root, 15 grams of cortex moutan, 25 grams of radix *rehmanniae*, 15 grams of Guang *lumbricus*, 10 grams of *panax pseudoginseng* and 15 grams of rhizoma *acori tatarinowii* |

3. Curative effect evaluation criteria: According to the changes of NIHSS scores before and after treatment, the curative effects of each group and the comparison among groups are evaluated. Curative effect evaluation criteria:
basic cure: NIHSS reduces by ≥90%;
significant improvement: NIHSS reduces by 46% to 89%;
improvement: NIHSS reduces by 18% to 45%;
no change: NIHSS reduces or increases by <18%;
deterioration: NIHSS increases by ≥18%.

Marked effective rate=basic cure rate+significant improvement rate; and total effective rate=basic cure rate+significant improvement rate+improvement rate.

Statistical treatment is performed by using the t test and the Fisher test.

4. Comparison of clinical effects among the seven groups is shown in Table 4:

TABLE 4

Comparison of the curative effects of seven groups of patients in acute stage of cerebral infarction (example)

| Groups | Number of patients | Basic cure | Significant improvement | Improvement | No change | Deterioration |
| --- | --- | --- | --- | --- | --- | --- |
| Patent prescription treatment group | 51 | 12 | 29 | 9 | 1 | 0 |
| Similar prescription treatment group 1 | 51 | 6 | 19 | 16 | 6 | 4 |

TABLE 4-continued

Comparison of the curative effects of seven groups of patients in acute stage of cerebral infarction (example)

| Groups | Number of patients | Basic cure | Significant improvement | Improvement | No change | Deterioration |
|---|---|---|---|---|---|---|
| Similar prescription treatment group 2 | 51 | 7 | 20 | 13 | 8 | 3 |
| Similar prescription treatment group 3 | 51 | 10 | 26 | 8 | 6 | 1 |
| Similar prescription treatment group 4 | 51 | 7 | 19 | 16 | 5 | 4 |
| Control group 1 (CN106110178A) | 51 | 9 | 27 | 7 | 6 | 2 |
| Control group 2 (CN101721572A) | 51 | 10 | 25 | 10 | 4 | 2 |

The comparison of clinical curative effects of the seven groups of patients is shown in Table 5:

TABLE 5

Comparison of clinical curative effects of seven groups of patients

| Groups | Marked effective | Effective | No effect | Marked effective rate (%) | Effective rate (%) |
|---|---|---|---|---|---|
| Patent prescription treatment group | 41 | 50 | 1 | 80.39 | 98.04 |
| Similar prescription treatment group 1 | 25 | 41 | 10 | 49.02 | 80.39 |
| Similar prescription treatment group 2 | 27 | 40 | 11 | 52.94 | 78.43 |
| Similar prescription treatment group 3 | 36 | 44 | 7 | 70.59 | 86.27 |
| Similar prescription treatment group 4 | 26 | 42 | 9 | 50.98 | 82.35 |
| Control group 1 (CN106110178A) | 36 | 43 | 8 | 70.59 | 84.31 |
| Control group 2 (CN101721572A) | 35 | 45 | 6 | 68.63 | 88.23 |

The comparison of NIHSS scores of the seven groups is shown in Table 6:

TABLE 6

Comparison of NIHSS scores of seven groups of patients

| Groups | Number of patients | Before treatment ($\bar{x} \pm s$) | After treatment ($\bar{x} \pm s$) |
|---|---|---|---|
| Patent prescription treatment group | 51 | 15.54 ± 1.76 | 4.66 ± 1.09 |
| Similar prescription treatment group 1 | 51 | 15.39 ± 1.80 | 5.71 ± 1.16 |
| Similar prescription treatment group 2 | 51 | 15.07 ± 1.66 | 5.78 ± 1.17 |
| Similar prescription treatment group 3 | 51 | 15.78 ± 1.70 | 5.10 ± 0.83 |
| Similar prescription treatment group 4 | 51 | 15.68 ± 1.78 | 6.22 ± 1.62 |
| Control group 1 (CN106110178A) | 51 | 15.61 ± 1.59 | 5.49 ± 1.14 |
| Control group 2 (CN101721572A) | 51 | 15.37 ± 1.73 | 5.02 ± 0.73 |

As shown in the above tables, the effective rate of the patent prescription treatment group is 98.04%, the effective rate of the similar prescription treatment group 1 is 80.39%, the effective rate of the similar prescription treatment group 2 is 78.43%, the effective rate of the similar prescription treatment group 3 is 86.27%, the effective rate of the similar prescription treatment group 4 is 82.35%, the effective rate of the control group 1 is 84.31%, the effective rate of the control group 2 is 88.23%, and there is a significant difference between the patent prescription treatment group and the other groups ($P<0.05$, the patent prescription treatment group is significantly better than the other groups). The marked effective rate of the patent prescription treatment group is 80.39%, the marked effective rate of the similar prescription treatment group 1 is 49.02%, the marked effective rate of the similar prescription treatment group 2 is 52.94%, the marked effective rate of the similar prescription treatment group 3 is 70.59%, the marked effective rate of the similar prescription treatment group 4 is 50.98%, the marked effective rate of the control group 1 is 70.59%, the marked effective rate of the control group 2 is 68.63%, and there is significant difference between the patent prescription treatment group and the other groups ($P<0.05$, the patent prescription treatment group is significantly better than the other groups). The above curative results show that the traditional Chinese medicine composition of the present invention has a good auxiliary effect on the restoration of neurological functions of patients in the acute stage of cerebral infarction and especially has obvious advantages in marked effective rate compared with other prescriptions, and the traditional Chinese medicine composition of the present invention can be used together with clinical treatment to improve the clinical symptoms and physical signs of the patients in the acute stage of cerebral infarction, demonstrating that the traditional Chinese medicine composition of the present invention has good curative effects on the patients in the acute stage of cerebral infarction and has potential clinical application value.

What is claimed is:

1. A method for treating a cerebral infarction comprising a step of administrating an effective amount of a herb composition to a subject in need, wherein the herb composition is prepared from the following raw materials in parts by weight: 10-50 parts of buffalo horns, 10-30 parts of unprocessed rehmannia roots, 10-30 parts of red paeony roots, 10-30 parts of cortex moutan, 6-20 parts of grassleaf sweetflag rhizome and 10-30 parts of turmeric root-tuber; wherein the cerebral infarction is an acute stage of the cerebral infarction.

2. The method according claim 1, wherein the herb composition is prepared from the following raw materials in parts by weight: 10-30 parts of buffalo horns, 10-20 parts of unprocessed rehmannia roots, 10-20 parts of red paeony roots, 10-20 parts of cortex moutan, 6-15 parts of grassleaf sweetflag rhizome and 10-20 parts of turmeric root-tuber.

3. The method according claim 1, wherein the herb composition is formulated into a preparation with pharmaceutically acceptable adjuvant materials.

4. The method according claim 3, wherein a form of the herb composition is a decoction, a granule, a capsule or a tablet.

5. The method according claim 1, wherein the herb composition is prepared by the following steps: mixing herbal pieces of the buffalo horns, the unprocessed rehmannia roots, the red paeony roots and the cortex moutan and extracting with water for 1-3 hours, concentrating into a water extract; mixing herbal pieces of the grassleaf sweetflag rhizome and the turmeric root-tuber and extracting with 70% ethanol for 1-2 hours, concentrating into an ethanol extract; mixing the water extract and the ethanol extract, drying.

6. The method according claim 5, wherein the amount of water is 8-10 times of the total weight of the the buffalo horns, the unprocessed rehmannia roots, the red paeony roots and the cortex moutan; extracting for 2-3 times.

7. The method according claim 5, wherein the amount of ethanol is 8-10 times of the total weight of the grassleaf sweetflag rhizome and the turmeric root-tuber; extracting for 2-3 times.

\* \* \* \* \*